(12) United States Patent
Holland et al.

(10) Patent No.: US 7,300,414 B1
(45) Date of Patent: Nov. 27, 2007

(54) TRANSCRANIAL ULTRASOUND THROMBOLYSIS SYSTEM AND METHOD OF TREATING A STROKE

(75) Inventors: Christy K. Holland, Cincinnati, OH (US); Daniel S. Kanter, Cincinnati, OH (US); Lawrence J. Busse, Mitchell, KY (US); Kenneth R. Wagner, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 439 days.

(21) Appl. No.: 10/111,722

(22) PCT Filed: Nov. 1, 2000

(86) PCT No.: PCT/US00/30104

§ 371 (c)(1),
(2), (4) Date: Apr. 26, 2002

(87) PCT Pub. No.: WO01/32258

PCT Pub. Date: May 10, 2001

Related U.S. Application Data

(60) Provisional application No. 60/241,986, filed on Oct. 20, 2000, provisional application No. 60/162,976, filed on Nov. 1, 1999.

(51) Int. Cl.
*A61B 17/20* (2006.01)
(52) U.S. Cl. ............................................ 604/22
(58) Field of Classification Search .............. 604/22, 604/119, 120; 600/437, 439, 442, 459, 469; 607/109
See application file for complete search history.

(56) References Cited

U.S. PATENT DOCUMENTS

| 5,080,101 | A |   | 1/1992  | Dory |
|-----------|---|---|---------|------|
| 5,217,018 | A | * | 6/1993  | Dias ............................ 600/463 |
| 5,307,816 | A |   | 5/1994  | Hashimoto et al. |
| 5,313,944 | A | * | 5/1994  | Crowley et al. ............. 600/409 |
| 5,399,158 | A |   | 3/1995  | Lauer et al. |
| 5,509,896 | A |   | 4/1996  | Carter |
| 5,648,098 | A |   | 7/1997  | Porter |
| 5,695,460 | A |   | 12/1997 | Siegel et al. |
| 5,713,848 | A |   | 2/1998  | Dubrul et al. |
| 5,807,258 | A | * | 9/1998  | Cimochowski et al. ..... 600/454 |
| 5,879,314 | A |   | 3/1999  | Peterson et al. |

(Continued)

OTHER PUBLICATIONS

"Low-Frequency, Low-Intensity Ultrasound Accelerates Thrombolysis Through The Skull"; *Ultrasound in Med. & Biol.*, vol. 25, No. 2, pp. 269-273, Feb. 1999.

(Continued)

*Primary Examiner*—Michael J. Hayes
(74) *Attorney, Agent, or Firm*—Dinsmore & Shohl LLP; Denise M. Everett

(57) ABSTRACT

A method of transcranial ultrasound thrombolysis comprises the steps of providing a predetermined level of ultrasonic energy substantially throughout a primary treatment zone encompassing the M1 branch and M2 branches of the middle cerebral artery of an individual. A thrombolytic agent is also administered to the individual. A transcranial ultrasound thrombolysis system (10) is also provided that includes a transducer (20). The transducer is adapted to provide a predetermined level of ultrasonic energy substantially throughout a primary treatment zone encompassing at least a substantial portion of the M1 branch and the M2 branches of the middle cerebral artery in one hemisphere of a brain.

31 Claims, 3 Drawing Sheets

U.S. PATENT DOCUMENTS

| | | | |
|---|---|---|---|
| 5,944,687 A * | 8/1999 | Benett et al. | 604/22 |
| 6,113,558 A | 9/2000 | Rosenschein et al. | |
| 6,176,842 B1 * | 1/2001 | Tachibana et al. | 604/22 |
| 6,537,246 B1 * | 3/2003 | Unger et al. | 604/82 |

OTHER PUBLICATIONS

"Focusing of Therapeutic Ultrasound Through a Human Skull: A Numerical Study"; *J. Acoust. Soc. Am.* 104 (3), Pt. 1, Sep. 1998, pp. 1705-1715.

"Low-Frequency Ultrasound Penetrates the Cranium and Enhances Thrombolysis In Vitro", *Neurosurgery*, vol. 43, No. 4, pp. 828-833; Oct. 1998.

"Trans-skull Ultrasound Therapy: The Feasibility of Using Image-Derived Skull Thickness Information to Correct the Phase Distortion"; *IEEE Transactions On Ultrasonics, Ferroelectrics, and Frequency Control*, vol. 46, No. 3, pp. 752-755; May 1999.

"Enhancement Of Thrombolysis By Ultrasound"; *Ultrasound in Med. & Biol.*, vol. 20, No. 4, pp. 375-382, 1994.

"Enhancement of Fibrinolysis In Vitro by Ultrasound"; *J. Clin. Invest. Enhanced Fibrinolysis with Ultrasound*, vol. 90, pp. 2063-2068; Nov. 1992.

"Ultrasound Accelerates Transport Of Recombinant Tissue Plasminogen Activator Into Clots", *Ultrasound in Med. & Biol.*, vol. 21, No. 3, pp. 419-424; 1995.

Characterization of Ultrasound-Potentiated Fibrinolysis In Vitro; *Blood*, vol. 81, No. 10, pp. 2636-2643; May 15, 1993.

\* cited by examiner

TRANSCRANIAL ULTRASOUND THROMBOLYSIS SYSTEM AND METHOD OF TREATING A STROKE

CROSS-REFERENCES TO RELATED APPLICATIONS

This application claims the benefit of U.S. Provisional Application No. 60/162,976 filed Nov. 1, 1999 and U.S. Provisional Application No. 60/241,986 filed Oct. 20, 2000, each of which disclosures are herein incorporated by reference.

TECHNICAL FIELD OF THE INVENTION

The present invention is directed generally to a transcranial ultrasound thrombolysis system and method for transcranial ultrasound thrombolysis and, more specifically, to a system and method of using ultrasonic energy in combination with a thrombolytic agent to assist in dissolving intracranial thrombi and to enhance the efficacy of a thrombolytic agent.

BACKGROUND OF THE INVENTION

Seven hundred thousand strokes occur each year in the United States alone and many result in death. Ischemic strokes are generally caused by an occlusion or blockage (either partial or complete) resulting from a blood clot in one of the blood vessels in the head. Successful treatment of stroke patients depends on early recognition of the stroke, and almost immediate treatment, such as within three to four hours of the onset of the stroke.

Currently, one treatment for acute ischemic stroke patients is the use of a specific dose of the thrombolytic agent recombinant tissue plasminogen activator, commonly known as rt-PA, administered intravascularly. However, this treatment is not commonly administered due to a variety of factors. The treatment may not be administered because of a delay in recognizing and diagnosing stroke symptoms and transporting stroke patients to an appropriate medical facility. In addition, physicians are often reluctant to administer rt-PA due to the increased risk of an intracerebral hemorrhage. Accordingly, hospitals are less likely to use rt-PA on an acute stroke patient if they do not have a specialized stroke neurologist present to diagnose correctly the need for rt-PA and address any subsequent complications.

As can be seen, current treatments have a number of shortcomings that can greatly reduce the availability of treatments for acute stroke patients. The current medical treatment is generally not used by front-line medical personnel. Such treatments can also have adverse side effects, and can have limited use and application. A need exists for a system and treatment method for providing quicker and/or easier treatment for acute ischemic stroke patients and/or for improving the efficacy of thrombolytic medicines, such as rt-PA, and reducing undesirable side effects.

SUMMARY OF THE INVENTION

It is an object of the present invention to provide a system and method for the treatment of strokes that addresses and overcomes the above-mentioned shortcomings and problems.

Another object of the present invention is to provide a system and method for the treatment of strokes that can be administered as soon as possible at the onset of stroke without a need for radiologic or imaging guidance to determine the specific vascular location of a clot.

Still another object of the present invention is to provide a system and method for the treatment of strokes that can be administered by front line medical personnel.

Still another object of the present invention is to provide a system and method for the treatment of strokes that avoid and/or reduce undesirable bioeffects, either cavitational, mechanical or thermal in nature.

To achieve the foregoing and other objects, and in accordance with the purpose herein, one embodiment of the present invention comprises a method of intracranial thrombolysis comprising the steps of providing a predetermined level of ultrasonic energy substantially throughout a primary treatment zone encompassing at least a substantial portion of the M1 branch and the M2 branches of the middle cerebral artery in one hemisphere of a brain of an individual and further administering a thrombolytic agent to the individual.

To achieve further objects and in accordance with the purposes herein, another embodiment of the invention is directed to a thrombolytic device comprising a transducer adapted to provide a predetermined level of ultrasonic energy substantially throughout a primary treatment zone encompassing at least a substantial portion of the M1 branch and the M2 branches of the middle cerebral artery in one hemisphere of a brain.

The method and system are advantageous in providing for relatively quick treatment of stroke without requiring radiologic or imaging guidance to determine a specific vascular location of a clot. Still other advantages and objects of the present invention will become apparent to those skilled in the art from the following description wherein there are shown and described alternative exemplary embodiments of this invention. As will be realized, the invention is capable of other different, obvious aspects, objects and embodiments, all without departing from the scope of the invention. Accordingly, the drawings, objects and descriptions should be regarded as illustrative and exemplary in nature only, and not as restrictive.

BRIEF DESCRIPTION OF THE DRAWINGS

While the specification concludes with claims particularly pointing out and distinctly claiming the present invention, it is believed the same will be better understood from the following description taken in conjunction with the accompanied drawings in which:

DETAILED DESCRIPTION OF THE PREFERRED EMBODIMENTS

Figure 1:
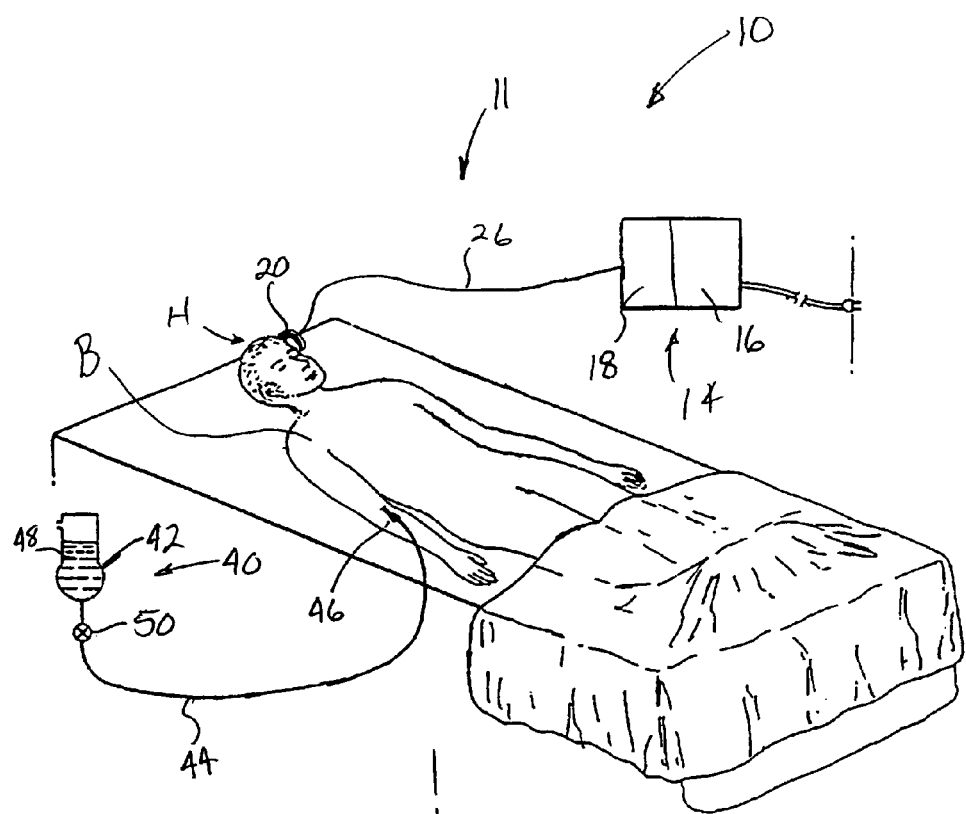
FIG. 1 is a schematic diagram of a transcranial ultrasonic thrombolysis system in accordance with the teachings of the present invention.

Referring now to the drawings in detail, wherein like numerals indicate the same elements throughout the figures, FIG. 1 exemplifies a system 10 for assisting in dissolving intracranial thrombi and for enhancing the thrombolytic action of a thrombolytic agent. The system 10 comprises a transducer 20 which is described in further detail below. As shown in FIG. 1, the system 10 may further include an ultrasound system 11 and may be used in combination with a medicine delivery system 40. The ultrasound system 11 used with the present invention can include an ultrasonic driver 14 for generating electrical energy that can be converted to ultrasound waves or energy at transducer 20. Driver 14 may be of a conventional design with an adjustable frequency generator 16 and/or an adjustable power amplifier 18. The driver 14 should be such that the ultrasound waves or energy are suitable and can be selected to penetrate the temporal bone of the head (H), and to be transmitted through cranial tissue without generating undesirable thermal, mechanical or cavitational effects. A frequency generator 16 used with the present invention should have an adjustable frequency range preferably from about 100 kHz to about 1 MHZ. The power amplifier 18 used with the present invention should also have an adjustable range up to about 150 W, and/or provide up to about 60 dB of gain. Also, the driver 14 should have an adjustable duty cycle from about 10% to 100% so that the wave operation can be pulsating, continuous, or both, as desired.

Transducer 20 is preferably electrically connected to the ultrasonic driver 14 by an electrical cord 26. Transducer 20 may be configured for converting electricity from an electrical source (e.g., ultrasonic driver 14) into ultrasound waves or energy, and for radiating or directing such ultrasonic waves or energy into the head (H). Use of the transducer 20, along with the medicine delivery system 40, should assist in dissolving or removing the blockage or occlusion in the cerebral blood vessel, and/or enhancing the efficacy of the dose of medicine (e.g., thrombolytic agent) being used. The size and configuration of transducer 20 used with the present invention should be selected so that ultrasound waves or energy, and preferably low energy ultrasound waves, can penetrate the temporal bone. Furthermore, the transducer 20 should be configured such that undesirable heat energy and cavitation effects are not created. Undesirable attenuating and heating of tissue may result with relatively high ultrasound frequencies. Frequencies that are too low penetrate the tissue but may cause cavitation and tissue damage. Suitable frequency ranges emitted by the transducer 20 can be from about 100 kHz to about 1 MHZ. In one example, the transducer 20 can emit frequencies from about 100 kHz to about 250 kHz. In another particular example, the frequency range of the transducer is about 120 kHz. Accordingly, it is desirable to select frequencies sufficiently low to minimize or prevent attenuation and heating of tissue while allowing sufficient penetration of tissue including the temporal bone. In addition, the selected frequency should not be low enough to cause cavitation and tissue damage at similar amplitudes. Also, the transducer 20 should be sized and configured so that it can deliver an intensity range from about 0.5 W/cm$^2$ to about 10 W/cm$^2$. In another embodiment, the transducer 20 can deliver an intensity range up to about 2 W/cm$^2$.

Figure 2:
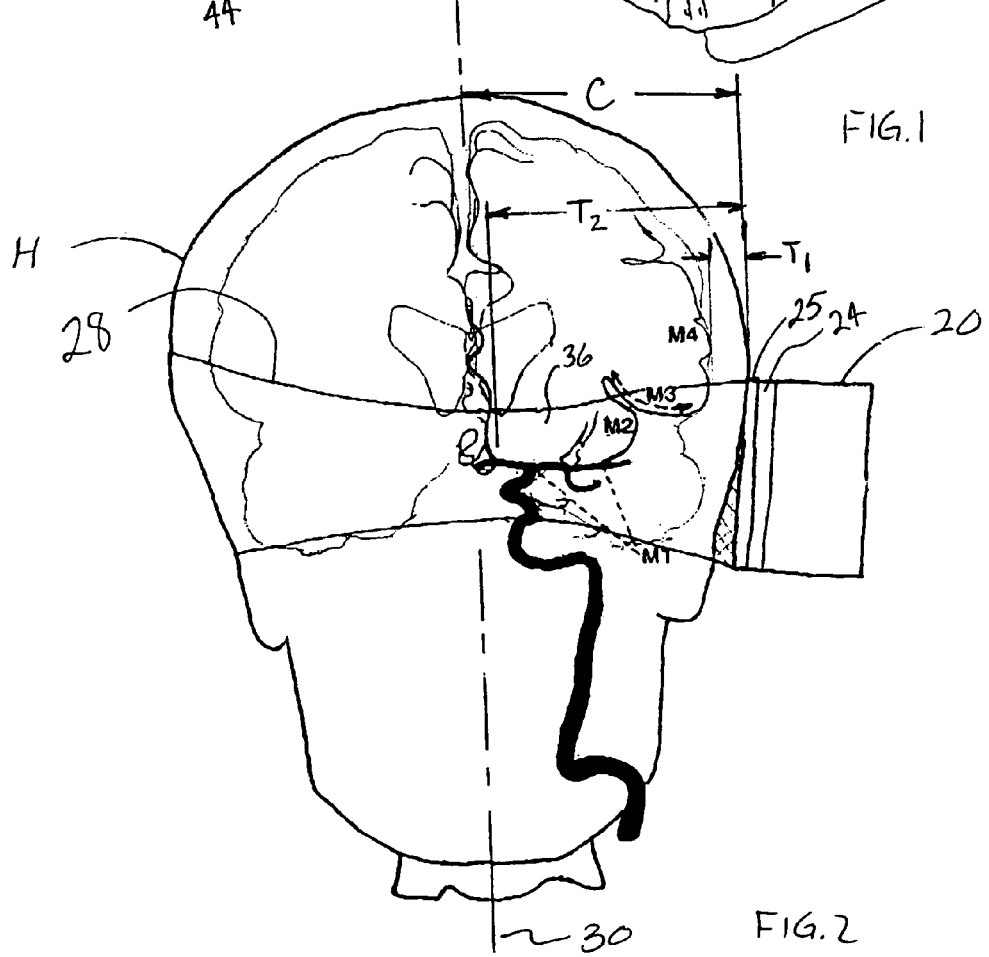
FIG. 2 is a vertical cross-sectional view of a transducer employed in a system of the present invention placed adjacent the head.
Figure 3:
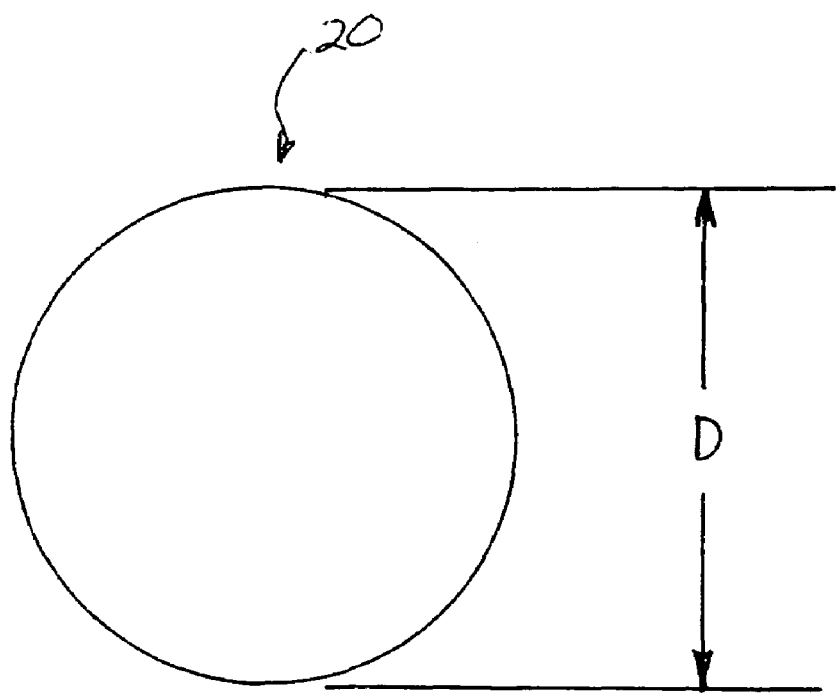
FIG. 3 is a front elevational view of a transducer employed in a system in accordance with the present invention.
Figure 5:
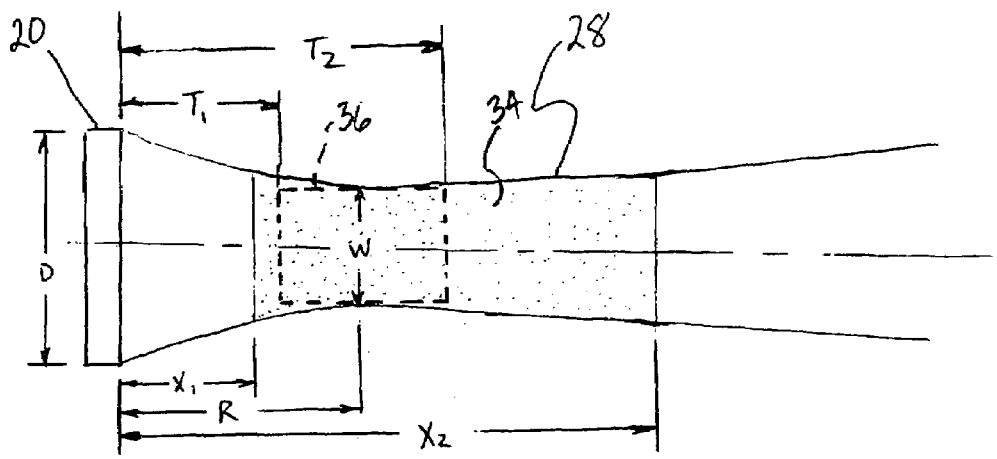
FIG. 5 is an elevational view of an exemplary transducer employed in a system in accordance with the present invention, with a corresponding beam profile.

A tip including a quarter-wave matching layer and/or a lens 24 may optionally be provided in a front portion of the transducer 20, such as the end portion of the transducer 20, for efficiently coupling ultrasound waves or energy into the head and/or focusing, concentrating or specifically directing ultrasound waves or energy to a desired area or volume in the body. In one embodiment, a predetermined level of ultrasonic energy is provided substantially throughout a primary treatment zone 36 encompassing at least a substantial portion of the M1 branch and M2 branches of the middle cerebral artery as shown in FIGS. 2 and 5. In other embodiments, the primary treatment zone 36 includes at least a substantial portion of the M3 branch other extravascular thrombi, or other intracranial vascular thrombi. Tip 24 should be sized and configured to optimize the transmission of ultrasound energy or waves through the temporal bone. As shown in FIG. 3, the transducer 20 may have a diameter or aperture greater than about 2 cm. In one embodiment, the transducer 20 may also have a diameter or aperture greater than about 5 cm. In still another embodiment, the transducer 20 may have a diameter or aperture of about 6 cm.

A beam width from about 3 cm to about 4 cm may be provided to allow for variations and the differences in human anatomy and in the position of a blockage or occlusion. In one particular embodiment, a beam width of about 3 centimeters is provided. Accordingly, by providing a sufficiently large beam width, the system may provide a secondary treatment zone 34 that is effective to encompass the primary treatment zone 36, and therefore treat the majority of strokes without the need for imaging or other techniques to determine the specific vascular location of a thrombi.

Figure 6:
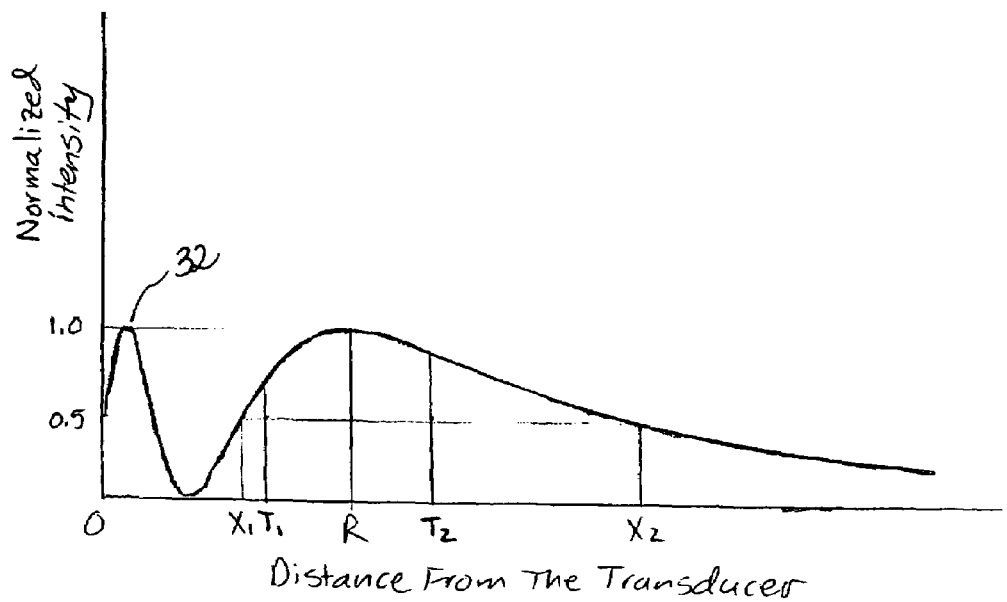
FIG. 6 is an axial beam profile of the normalized intensity versus distance from the transducer of an ultrasound beam in a system in accordance with the present invention.

One example of a suitable transducer 20 to assist in concentrating or specifically directing ultrasound waves or energy to the area or location of the middle cerebral artery area is a transducer having a diameter of about 6 cm and a pillbox shaped configuration made of a piezoelectric ceramic. In one example, the transducer 20 may be sized and configured to have a Rayleigh distance (R) as shown in FIGS. 5 and 6, which is generally the distance between the front of the transducer (e.g., located adjacent the skin above the temporal bone) and the location of the natural focus having the highest intensity from the ultrasonic waves.

FIG. 5 shows one example of a transducer 20 emitting a beam 28 of ultrasonic energy or waves. As illustrated in FIG. 5, the beam 28 of ultrasonic energy has a natural focus commonly known as the Rayleigh distance (R) from the transducer to the distance at which the intensity of the beam reaches its maximum. The Rayleigh distance (R) is determined by the operating frequency of the transducer 20, the dimensions of the transducer and the speed of sound through the medium in which the ultrasonic sound waves are traveling. With a transducer with circular cross-section (e.g., as illustrated in FIGS. 2 and 3) the following relationship exists:

$$R = (f/a)(D/2)^2$$

wherein:
R=Rayleigh distance
f=Operating frequency of the transducer
D=Diameter of the transducer
a=speed of sound through the cranial tissue.

As shown in FIG. 6, an exemplary axial profile of the beam 28 is displayed. It is understood that the exact profile may vary depending on the medium in which the ultrasonic waves are traveling. For instance, the axial profile would show a decrease in intensity if the energy is attenuated when traveling through the medium (e.g., cranial tissues). The effective secondary treatment zone 34 is defined between the ($X_1$) and ($X_2$) positions. For example, FIG. 6 shows one embodiment where ($X_1$) and ($X_2$) are located at 50% of the maximum intensity. In this instance, a therapeutic effect may be achieved by exposing the thrombi to an intensity of at least 50% of the maximum intensity. Accordingly, a predetermined intensity level of ultrasonic energy may be provided to expose all of the secondary treatment zone to at least the predetermined level of ultrasonic energy. In one embodiment, as shown in FIGS. 5 and 6, the predetermined level is at least 50% of the maximum intensity. In other embodiments, the predetermined level is at least 75% of the maximum intensity level. In still other embodiments, the predetermined level is at least 90% or at least 95% of the maximum intensity level. It will be appreciated that intensity levels of less then 50% of the maximum level could be used.

As illustrated in FIG. 6, the relationship of intensity as a function of distance results in the distance between ($X_2$) and (R) being greater than the distance between ($X_1$) and (R). Accordingly, when locating the secondary treatment zone, the ultrasound system may be designed such that the Rayleigh distance (R) of the ultrasound beam is positioned at least substantially at the center of the primary treatment zone 36 as shown in FIGS. 5 and 6. Locating the Rayleigh distance (R) at the center maximizes the intensity of the ultrasonic energy at the center of the primary treatment zone 36. Alternatively, the beam 28 can be oriented such that the Rayleigh distance (R) is offset from the center of the primary treatment zone 36 and positioned closer to the transducer such that the intensity of the sound waves at ($T_1$) and ($T_2$) are approximately equal. This location of the beam would be useful to maximize the intensity of the sound waves at each location in the primary treatment zone 36. In still another embodiment, the beam can be positioned so that the center of the primary treatment zone 36 is located at the middle of the secondary treatment zone, i.e., midway between $X_1$ and $X_2$. This location of the beam would maximize the additional coverage beyond the normal primary treatment zone on each side to cover additional possible thrombi locations.

The concepts of the present invention may treat both sides of the brain at once. However, the invention is also useful to treat one side of the brain. It is understood that treating one side of the brain may also result in incidental treatment of the other side of the brain as well. Symptoms of the patient will indicate which side of the brain contains the thrombi. For example, paralysis or weakness on the right side of the body indicates the thrombi is located on the left side of the brain. The center line 30 (see FIG. 2) of an adult brain will typically be located a distance (C) of about 6 to 7½ centimeters from the transducer 20. In one embodiment, the primary treatment zone begins at a distance $T_1$ of about 2 centimeters from the transducer 20 and continues to a distance $T_2$ of about 7 centimeters from the transducer 20. In addition, the primary treatment zone width (W) throughout the primary treatment zone is from about 3 centimeters to about 4 centimeters. There is a very high probability that any intracranial thrombi will be located within this primary treatment zone.

In order to locate the secondary treatment zone 34 such that ($X_1$) and ($X_2$) encompass the primary treatment zone 36, the Rayleigh distance (R) should be from about 3 centimeters to about 6 centimeters. In another example, the Rayleigh distance (R) is about 6.2 centimeters.

In one embodiment, the beam width (W) of the beam between ($X_1$) and ($X_2$) is about 3 centimeters to about 4 centimeters. The beam width can be controlled by changing the diameter (D) or aperture of the transducer 20 while keeping the frequency fixed for example. The beam width (W) at the Rayleigh distance (R), otherwise known as the 3-dB beam width, is about half the diameter (D) of the transducer 20. Thus, a transducer 20 having a circular aperture with a diameter of about 6 centimeters will produce a beam having a 3-dB beam width of about 3 centimeters at the natural focus of the transducer. In embodiments wherein the treatment zone is exposed to ultrasonic energy at least half of the maximum ultrasonic energy, the half-intensity beam width will be between about 3 centimeters and 4 centimeters.

As shown in FIG. 6, one or more pre-focus high intensity spots 32 may exist in the beam profile. In certain embodiments, it might be desirable to reduce or eliminate these spots 32. For example, a conformal array transducer around part of the head (H) may be arranged to eliminate or reduce the spot 32.

To enhance and optimize insonification into the head (H), the transducer 20 may have a quarter wave matching layer. An integral gel pad 25 may be present for assisting in coupling an ultrasound energy or waves (US) to heads of different geometries.

The transducer 20 used with the present invention can be a transducer configured for transcranial use to minimize the invasiveness of the treatment as exemplified in FIG. 2.

A conventional cooling system may optionally be present in the transducer 20 employed in the method and system of the present invention to assist in preventing the surrounding body tissue from becoming burned or overheated due to the transfer and transmission of ultrasound waves or energy. A thermocouple may be mounted on the edge of the transducer 20 to permit temperature monitoring during use. Also, a cooling medium may be directed to the transducer 20 from a source away from the transducer 20, and the cooling medium may be either air or liquid.

Figure 4:
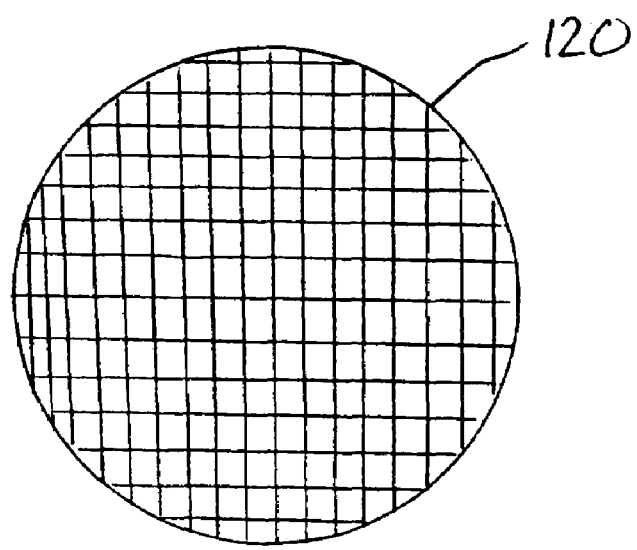
FIG. 4 is a front elevational view of a transducer in the form of a 2-dimensional array employed in a system in accordance with another embodiment of the present invention.

One or more transducers 20 may be used with the present invention, and each may be selectively adjusted to account for variations in head geometry. As shown in FIG. 4, the transducer 120 may comprise an array of transducers, such as a 2-dimensional conformal array. Individual elements of the array may be square, hexagonal, segmented rings, or any other pattern which fills the emitting area of the transducer and can be controlled by a suitably designed driver system. The beam can be characterized, with a focus for example, by the cumulative ultrasound emissions from each of the individual transducers in the array.

The system of the present invention may also include a holding device to assist in appropriately positioning the transducer 20 on the head (H) to enhance its effect on an intracranial circulatory system, and in particular, the middle cerebral artery area. Furthermore, the holding device should be configured for maintaining the transducer's 20 desired position during use and treatment to enhance the effect and/or efficacy of the ultrasound waves or energy. Suitable examples of such devices may include a head harness, straps, frames, helmets, and the like. The transducer 20 may be releasably detached, or permanently affixed to the holding device.

The medicine delivery system 40 can include any conventional intravascular IV delivery system for the delivery of fluids into the circulatory system of the body B. The thrombolytic agent or solution 48 is generally housed in a container 42, such as an IV bag or bottle, and is in fluid communication to the body B via a catheter 44. Solution 48 is preferably injected and delivered intravascular into the body B with a needle 46 having an appropriate gauge, such as an 18-22 gauge needle.

The solution or thrombolytic agent 48 used with the present invention can be any solution or medicine used to assist in the removal cerebral vessel blockages or obstructions, such as a blood clot, or to enhance the thrombolytic action in a blocked cerebral vessels. A suitable example of a solution or thrombolytic agent 48 used with the present invention may include an appropriate solution or suitable dose of a thrombolytic drug.

Any thrombolytic agent or anti-platelet drug can be used with the present invention. Illustrative examples of suitable agents for use in alleviating cerebral blood clots, or other blockages or occlusions which might be used with the present invention include recombinant tissue plasminogen activator, for example rt-PA. In another example, abciximab or other antiplatelet agents are used. A suitable dosage or concentration of rt-PA may be about 0.9 mg per kg of body weight. About 10% of the dosage is preferably given as a bolus at the onset of treatment, and the remaining portion is preferably given over the period of about an hour. Alternatively, a suitable dosage or concentration of rt-PA used with the present invention may be less than 0.9 mg per kg of body weight.

In an alternative embodiment, the thrombolytic agent (e.g., t-PA) may be encapsulated or otherwise contained in a medium that is sufficiently protective so that the thrombolytic agent can be delivered to the body (B) and transmitted through the circulatory system without effecting nontargeted areas. The protective medium is capable of being ruptured or otherwise exposing the thrombolytic agent by the ultrasound waves or energy generated by the ultrasound device 11 used with the present invention. This arrangement will target the exposure of the thrombolytic agent to the affected area, thereby minimizing adverse affects in other parts of the body. Suitable examples of such encapsulating materials include microballoons made of a cross-linked albumin, a lipid vehicle and a targeting moiety, or other protein compatible with blood products. The size of the encapsulation should be optimized to allow circulation of the encapsulated drug throughout the body (e.g., including the lungs) and yet be readily destroyed by the application of external ultrasound. In still another embodiment, the present invention may use targeted gas-filled echocontrast agents to act as cavitation nuclei at the site of the clot.

In use, the present invention can be used to treat acute stroke patients. Once a decision is made to administer a course of treatment, the medicine delivery system 40 is intravenously connected to the body (B) of a patient. More specifically, the needle 46 can be inserted through the skin and is inserted into the circulatory system. Preferably, the needle 46 is inserted into a suitable artery or vein so that the solution 48 is quickly and efficiently directed to the site of the obstruction or clot. Exemplary vessels include the radial vein (e.g., see FIG. 1), antecubital vessels, subclavian vein, femoral vein, or femoral artery. Once the needle 46 is appropriately inserted and securely positioned, a valve 50 may be switched to the open position so that the solution 48 can flow from the container 42, through a catheter 44, through the needle 46, and into the body B.

As exemplified in FIG. 2, the transducer 20 may be placed near or adjacent the head (H) of the body (B), and preferably, near or adjacent the temple. In particular, the transducer 20 is selected, positioned, and activated with a natural focus having a Rayleigh distance (R) from about 3 centimeters to about 6 centimeters such that the secondary treatment zone 34 will encompass a zone 36 that has a high probability of containing a thrombus as shown in FIGS. 5 and 6.

The driver 14 can be connected to an electrical source, activated, or turned on, and an electrical current is transmitted through the cord 26 to the transducer 20. The electrical energy is converted or transformed to ultrasound waves or energy at the transducer 20. The resulting ultrasound energy or waves are emitted, provided or directed into the body B, preferably through the temporal bone and toward the blockage or occlusion (e.g., blood clot), such as within the middle cerebral artery. The transducer 20 can radiate, direct, emit or provide ultrasound waves or energy (US) at a frequency range from about 100 kHz to about 1 MHZ, such as from about 100 kHz to about 250 kHz. In one particular embodiment, the frequency of the transducer is about 120 kHz. The amplitude, or intensity, of the sound waves are from about 0.5 W/cm$^2$ to about 10 W/cm$^2$. In one embodiment, the amplitude or intensity might be up to 2 W/cm$^2$, as desired. The duty cycle of the ultrasound waves or energy may be adjustable, as desired, and can be set at a range from about 10% to 100% (or continuous wave). The ultrasound waves or energy are radiated, directed, emitted and directed during the period that the solution 48 is being administered intravenously. The ultrasound waves or energy may be radiated, directed, emitted and directed for about an hour, although larger or smaller time periods may be employed.

In a preferred embodiment, a transducer 20 may also be fixed in the desired position near or adjacent the temple of the head using a strap, or other affixation device.

It will be appreciated that the system 10 and methods described herein are useful in the lysis of intracranial thrombi. The application of ultrasonic energy to a primary treatment zone allows increased efficacy of thrombolytic agents. Accordingly, in some embodiments of the present invention, the techniques described herein will result in a reduced dosage of thrombolytic agent, thereby reducing possible occurrences of undesirable side effects such as hemorrhage complications. In addition, the device and methods described herein provide an ultrasonic zone that targets the primary zone. Accordingly, therapy may be initiated sooner since there is no need for radiologic or imaging guidance to determine the exact vascular location of the thrombi.

The portability and ease of use of the device may even allow treatment to begin before arrival at the hospital. For instance, emergency technicians may start therapy on site and/or may administer therapy on an ambulance for example.

Having shown and described the preferred embodiments to the present invention, further adaptations of the present invention as described herein can be accomplished by appropriate modifications by one of ordinary skill in the art without departing from the scope of the present invention. For example, other thrombolytics may be used with the present invention. In addition, while certain transducers shown and described throughout this application have circular section, it is understood that they could be formed with other shapes including polygons (e.g., triangle, square, or other polygon with four or more sides), elliptical, or other geometric shapes. In addition, other methods of providing a secondary treatment zone can involve focusing the beam with a spherical segment for example, attaching or forming the transducer with a lens, a conformal 2-dimensional array, and/or forming a helmet to receive the transducers to place over the head. Several such potential modifications have been discussed and others will be apparent to those skilled in the art. Accordingly, the scope of the present invention should be considered in terms of the following claims and is understood not to be limited in the details, structure and operation shown and described in its specification and drawings.

We claim:

1. A method of transcranial ultrasound thrombolysis comprising the steps of:
    a) non-invasively providing a predetermined level of ultrasonic energy substantially throughout a primary treatment zone encompassing at least a substantial portion of the M1 branch and M2 branches of the middle cerebral artery in one hemisphere of a brain of a patient; and
    b) administering a thrombolytic agent to the individual, wherein the predetermined level of ultrasonic energy is provided by a transducer and the transducer produces an ultrasonic frequency of from about 100 kHz to 1 MHz.

2. The method of claim 1 wherein the transducer is placed adjacent the head of the individual.

3. The method of claim 2, wherein the transducer comprises an array of transducers to create the primary zone.

4. The method of claim 3, wherein the array of transducers comprises a 2-dimensional conformal array.

5. The method of claim 2, wherein the transducer is provided with a circular cross-section including a diameter of about 6 centimeters.

6. The method of claim 2, wherein the ultrasonic energy is emitted with a Rayleigh distance from about 3 centimeters to about 6 centimeters.

7. The method of claim 2, wherein the ultrasonic energy is emitted with a Rayleigh distance that locates the natural focus in one hemisphere of the brain.

8. The method of claim 2, wherein the transducer is located adjacent to one side of the skull such that the ultrasonic energy is emitted as a beam of energy with a Rayleigh distance that locates the natural focus in one hemisphere of the brain adjacent the one side of the skull.

9. The method of claim 8, wherein the transducer produces an ultrasonic frequency of from about 100 kHz to about 250 kHz.

10. The method of claim 9, wherein the transducer produces an ultrasonic frequency of about 120 kHz.

11. The method of claim 1, wherein the ultrasonic energy is provided as a beam of energy with a beam width from about 3 centimeters to about 4 centimeters.

12. The method of claim 1, wherein the ultrasonic energy is provided as a beam of energy with a beam width of about 3 centimeters at the natural focus.

13. The method of claim 1, wherein the thrombolytic agent comprises rt-PA.

14. The method of claim 1, wherein the primary treatment zone further encompasses at least a portion of the M3 branches of the middle cerebral artery.

15. The method of claim 1, wherein the thrombolytic agent is activated by a predetermined level of ultrasonic energy.

16. The method of claim 15, wherein the thrombolytic agent is contained by a protective material that allows the thrombolytic agent to be released when exposed to a predetermined level of ultrasonic energy.

17. A transcranial ultrasound thrombolysis system comprising:
    a transducer adapted to be placed adjacent to an exterior surface of a cranium; and
    an ultrasonic driver adapted to generate energy that can be converted at the transducer to ultrasonic energy suitable for penetrating the cranium and transmitting through cranial tissue without generating undesirable thermal, mechanical or cavitational effects,
    wherein the system is adapted to non-invasively provide a predetermined level of ultrasonic energy substantially throughout a primary treatment zone encompassing at least a substantial portion of the M1 branch and the M2 branches of the middle cerebral artery in one hemisphere of a brain, and further wherein the transducer provides an ultrasonic frequency of from about 100 kHz to about 1 MHz.

18. The system of claim 17, wherein the transducer comprises an array of transducers adapted to create a secondary treatment zone.

19. The system of claim 17, wherein the transducer has a diameter of about 6 centimeters.

20. The system of claim 17, wherein the primary treatment zone is adapted to further encompass at least a portion of the M3 branches of the middle cerebral artery of one hemisphere of a brain.

21. The system of claim 17, wherein the system is adjustable to vary the duty cycle of the ultrasonic energy.

22. The system of claim 21, wherein the system is adjustable to vary the duty cycle from about 10% to 100%.

23. The system of claim 17, wherein the system provides a duty cycle of the ultrasonic energy from about 10% to 100%.

24. The system of claim 17, wherein the transducer is adapted to produce ultrasonic frequencies of from about 100 kHz to about 250 kHz.

25. The system of claim 24, wherein the transducer is adapted to produce ultrasonic frequencies of about 120 kHz.

26. The system of claim 17, wherein the transducer is adapted to produce ultrasonic amplitudes of about 0.5 W/cm$^2$ to about 2 W/cm$^2$.

27. The system of claim 17, wherein the transducer is adjustable to select an ultrasonic amplitude.

28. The system of claim 27, wherein the transducer is adjustable to select an ultrasonic amplitude from about 0.5 W/cm$^2$ to about 2 W/cm$^2$.

29. The system of claim 17, wherein the transducer is adapted to emit ultrasonic energy in a general direction away from the transducer and toward the M1 branch and M2 branches of the middle cerebral artery such that the Rayleigh distance of the beam is from about 3 centimeters to about 6 centimeters from the transducer.

30. The system of claim 17, wherein the transducer is adapted to produce an ultrasonic beam width from about 3 centimeters to about 4 centimeters.

31. The system of claim 17, wherein the transducer is adapted to produce a width of about 3 centimeters at the natural focus.

* * * * *